US007349808B1

(12) United States Patent
Kreiswirth et al.

(10) Patent No.: US 7,349,808 B1
(45) Date of Patent: Mar. 25, 2008

(54) SYSTEM AND METHOD FOR TRACKING AND CONTROLLING INFECTIONS

(75) Inventors: Barry N. Kreiswirth, New York, NY (US); Steven M. Naidich, New York, NY (US)

(73) Assignee: Egenomics, Inc., New York, NY (US)

( * ) Notice: Subject to any disclaimer, the term of this patent is extended or adjusted under 35 U.S.C. 154(b) by 0 days.

(21) Appl. No.: 09/656,084

(22) Filed: Sep. 6, 2000

(51) Int. Cl.
*G01N 33/48* (2006.01)
*G06F 7/00* (2006.01)

(52) U.S. Cl. ............................. 702/19; 702/20; 703/11; 435/7.1; 436/501; 536/24.5

(58) Field of Classification Search .................. 702/19; 435/4, 6
See application file for complete search history.

(56) References Cited

U.S. PATENT DOCUMENTS

| | | | |
|---|---|---|---|
| 5,396,227 A * | 3/1995 | Carroll et al. | |
| 5,619,991 A * | 4/1997 | Sloane | 600/300 |
| 5,660,981 A | 8/1997 | Grosz et al. | 435/6 |
| 5,691,136 A | 11/1997 | Lupski et al. | 435/6 |
| 6,404,340 B1 * | 6/2002 | Paradiso et al. | 340/572.5 |

FOREIGN PATENT DOCUMENTS

WO    WO98/50555    11/1998

OTHER PUBLICATIONS

Frenay et al. Molecular Typing of Methicillin-Resistant *Staphylococcus aureus* on the Basis of Protein A Gene Polymorphism. Eur. J. Clin. Microbiol. Infect. Dis., 1996, vol. 15, pp. 60-64.*
Hoe et al. Rapd Molecular Genetic Subtyping of Serotype M1 Group A Streptococus Strains. Emerg. Infect. Dis. 1999, vol. 5, No. 2, pp. 254-263.*
Levitt. The US-EU Conference on Extension of the Salm/Enter-net Surveillance System for Human Salmonella and *Escherichia coli* O157 Infections. Emerg. Infect. Dis., 1998, vol. 4, No. 3, pp. 502-503.*
O'Brien et al. DNA Fingerprints From *Mycobacterium tuberculosis* Isolates of Patients Confined for Therapy Noncompliance Show Frequent Clustering. CHEST, 1997, vol. 112, No. 2, pp. 387-392.*
Griffiths et al., An Introduction to Genetic Analysis, W H Freeman & Co, pp. 1-3, 1999.*
Benson et al., Nucleic Acids Research, 1997, vol. 25, pp. 1-6.*
Belkum et al., Infection and Immunity, vol. 65, pp. 5017-5027, 1997.*
CDC Plan: Preventing Emerging Infectious Diseases; a strategy for the 21st Century: Oct. 1998, Atlanta, Ga. pp. 1-68.*
Enright et al. Multilocus Sequencing Typing. Trends in Microbio., Dec. 1999, vol. 7, No. 12, pp. 482-487, See p. 485, 1st column, paragraphs 3-4; and see bridging paragraph of pp. 485-486.
Greiser-Wilke et al. Structure and Presentation of a World Wide Web Database of CSF Virus Isolates Held at the EU Reference Laboratory. Vet. Microbio., 2000, vol. 73, pp. 131-136. See abstract.

Richet et al. Building Communication Networks: International Network for the Study and Prevention of Emerging Antimicrobial Resistance. Emerging Infect. Dis. Mar.-Apr. 2001, vol. 7, No. 2, pp. 319-322. See abstract.
Herminia de Lencastre et al., "Testing the Efficacy of a Molecular Surveillance Network: Methicillin-Resistant *Staphylococcus aureus* (MRSA) and Vancomycin-Resistant *Enterococcus faecium* (VREF) Genotypes in Six Hospitals in the Metropolitan New York City Area", Microbial Drug Resistance, vol. 2, No. 3, 1996, pp. 344-351.
R. Durbin et al., "Biological Sequence Analysis", Probablistic Models of Proteins and Nucleic Acids, 1998, pp. 17-19. The Press Syndicate of The University of Cambridge.
David Sankoff et al., "Time Warps, Sting Edits, and Macromolecules", The Theory and Practice of Sequence Comparison, CSLI Publications 1999, Chapter 2, Recognition of Patterns in Genetic Sequences, B. Ericksson et al., pp. 55-57.
Brian Spratt, "Multilocus Sequence Typing: Molecular Typing of Bacterial Pathogens in an Era of Rapid DNA Sequencing and the Internet", Microbiology 1999, 2, pp. 312-316.
Dan Gusfield, "Algorithms on Strings, Trees, and Sequences", 1999, pp. 215-219. The Press Syndicate of The University of Cambridge.
A. van Belkum et al., "Outbreak of Amoxicillin-Resistant *Haemophilus influenza* Type b: Variable Number of Tandem Repeats as Novel Molecular Markers," Journal of Clinical Microbiology, 35(6): 1517-1520 (1997).
A. van Belkum et al., "Variable Number of Tandem Repeats in Clinical Strains of *Haemophilus influenza*," Infection and Immunity, 65(12):5017-5027 (1997).
A. van Belkum et al., "Short-Sequence DNA Repeats in Prokaryotic Genomes," Microbiology and Molecular Biology Reviews, 62(2):275-293 (1998).
N. Kobayashi et al., "Analysis of genomic diversity within the Xr-region of the protein A gene in clinical isolates of *Staphylococcus aureus*," Epidermiol. Infect., 122:241-249 (1999).
Database EMBL 'Online!, AAX13101 *Enterococcus faecalis* genome contig SEQ ID No. 164, Mar. 19, 1999.
B. Shopsin et al., "Evaluation of Protein A Gene Polymorphic Region DNA Sequencing for Typing of *Staphylococcus aureus* Strains," J. Clin. Micr., 3556-3563 (1999).

(Continued)

Primary Examiner—Mary K. Zeman
(74) Attorney, Agent, or Firm—Bingham McCutchen LLP

(57) ABSTRACT

The present invention is a system and method for performing real-time infection control over a computer network. The method comprises obtaining a sample of a microorganism at a health care facility, sequencing a first region of a nucleic acid from the microorganism sample, comparing the first sequenced region with historical sequence data stored in a database, determining a measure of phylogenetic relatedness between the microorganism sample and historical samples stored in the database, and providing infection control information based on the phylogenetic relatedness determination to the health care facility, thereby allowing the health care facility to use the infection control information to control or prevent the spread of an infection.

33 Claims, 8 Drawing Sheets

OTHER PUBLICATIONS

B. Shopsin et al., "Use of Coagulase Gene (*coa*) Repeat Region Nucleotide Sequences for Typing of Methicillin-Resistant *Staphylococcus aureus* Strains," *J. Clin. Microbiol.*, 38(9):3453-3456 (2000).

A. van Belkum, "Short sequence repeats in microbial pathogenesis and evolution," *Cell, Mol. Life Sci.*, 56:729-734 (1999).

A. van Belkum, "The role of short sequence repeats in epidemiologic typing," *Current Opinion in Microbiol.*, 2(3) 306-311 (1999).

Richard Frothingham, *Journal of Clinical Microbiology*, Differentiation of Strains in *Mycobacterium tuberculosis* Complex by DNA Sequence Polymorphisims, Including Rapid Identification of M. bovis BCB, Apr. 1995, pp. 840-844.

Richard Frothingham, et al., *Microbiology*, Genetic diversity in the *Mycobacterium tuberculosis* complex based on variable numbers of tandem DNA repeats, 1998, 144, pp. 1189-1196.

Kathryn E. Stockbauer et al., *Proc. Natl. Acad. Sci. USA*, Hypervariability generated by natural selection in an extracellular complement-inhibiting protein of serotype M1 strains of group A. *Streptococcus*, Mar. 1998. vol. 95, pp. 3128-3133.

Nancy P. Hoe, et al., *Nature Medicine*, Rapid selection of complement-inhibiting protein variants in group A *Streptococcus* epidemic waves, Aug. 1999, vol. 5, No. 8, pp. 924-929.

European J. Clin. Microbiol. Infect. Dis., A. van Belkum et al. "Are Variable Repeats in the *spa* Gene Suitable Targets for Epidemiological Studies of Methicillin-Resistant *Staphylococcus aureus* Strants?", Letters, 1996, vol. 15, pp. 768-770.

European J. Clin. Microbiol. Infect. Dis., H.M.E. Frenay et al. "Molecular Typing of Methicillin-Resistant *Staphylococcus aureus* on the Basis of Protein A Gene Polymorphism", Article, 1996, vol. 15, No. 1, pp. 60-64.

European Respiratory J, M. Goyal et al., "Rapid detection of multidrug-resistant tuberculosis", 1997, vol. 10, pp. 1120-1124.

Proc. Natl. Acad. Sci., Martin C.J. Maiden et al., "Multilocus sequence typing: A portable approach to the identification of clones within populations of pathogenic microorganisms", Mar. 1998, vol. 95, pp. 3140-3145.

Emerging Infectious Diseases, Robert J. Rubin et al., "The Economic Impact of *Staphylococcus aureus* Infection in New York City Hospitals", Jan.-Feb. 1999, vol. 5, No. 1, pp. 9-17.

Journal of Clinical Microbiology, B. Shopsin et al., "Evaluation of Protein A Gene Polymorphic Region DNA Sequencing for Typing of *Staphlococcus aureus* Strains", Nov. 1999, vol. 37, No. 11, pp. 3556-3563.

Website: http//cpsweb.cps.ca/english/statements/ID/id99-03.htm, Infectious Diseases and Immunization committee, Canadian Paediatric Society (CPS), "Control of methicillin resistant *Staphylococcus aureus* in Canadian paediatric institutions is still a worthwhile goal", Jun. 12, 2000, pp. 1-8.

\* cited by examiner

| SPECIES | S. aureus | S. aureus |
|---|---|---|
| SUBSPECIES | A1' | B7" |
| SEQ REGION 1 | ATTCATAGAT... | ATTAATAGAT... |
| SEQ REGION 2 | CGTACTATCC... | CGTACTATCC... |
| SEQ REGION 3 | ATTCGTTATA... | ATTCGTTATA... |
| REGION 1 PRIMERS | | |
| REGION 2 PRIMERS | | |
| REGION 3 PRIMERS | | |
| REPEAT MOTIF RGN 1 | TKJMP.. | TKJMP.. |
| REPEAT MOTIF RGN 2 | ABABA... | ABBBA... |
| REPEAT MOTIF RGN 3 | TYYT.. | TYYT.. |
| DATE | June 5, 2000 | Dec 1, 1999 |
| PATIENT MEDICAL HISTORY | Hospitalized in New York Hospital, June 2000 for 3 weeks, heart surgery... | Hospitalized in Florida in 1996, treated for minor burns |
| PATIENT MEDICAL UPDATE INFO | Patient hospitalized 3 weeks for infection and released.... | Patient died due to infection after two weeks... |
| LOCATION | Mt. Sinai Hospital, Toronto, Burn Ward | New York City Hospital, ICU |

FIG. 7A

| S. AUREUS | | | |
|---|---|---|---|
| SEQ REGION | REPEAT 1 | REPEAT 2 | REPEAT 3 |
| PROTEIN A $X_R$ | AATTCGCCTAGG.. | AATTCCCCTAGG.. | TAGGCCGT... |
| REGION 2 | TTAAAGGCCTGA.. | GGTTCCAATAAT.. | GGTTAACC.. |
| REGION 3 | ... | ... | ... |

FIG. 7B

SYSTEM AND METHOD FOR TRACKING AND CONTROLLING INFECTIONS

BACKGROUND OF THE INVENTION

A major problem in hospitals and health care facilities today is the prevalence of hospital-acquired infections. Infections picked up in institutions are referred to as "nosocomial" infections. 5-10% of patients who enter a hospital for treatment will acquire a nosocomial infection from bacteria in the hospital environment. This translates to two million people per year. Nosocomial infections cause 90,000 deaths per year in the United States alone.

The most problematic bacterial infection in hospitals today is Staphylococcus aureus (S. aureus). S. aureus is the leading cause of nosocomial infection in the United States. In New York City (NYC), methicillin-resistant S. aureus (MRSA) accounts for approximately 29% of nosocomial infections and 50% of associated deaths. S. aureus also causes a variety of diseases including abscesses, blood stream infections, food poisoning, wound infection, toxic shock syndrome, osteomyelitis, and endocarditis.

S. aureus has become highly resistant to antibiotic therapies. In fact, vancomycin is the only effective treatment against most methicillin-resistant S. aureus strains. It is predicted that S. aureus will eventually develop resistance to vancomycin. Other species of bacteria have already developed resistance to vancomycin. High-level resistance to vancomycin exists in both Enterococcus faecalis and Enterococcus faecium, two gram-positive species that have previously exchanged resistance genes with S. aureus. It is therefore predicted that high-level resistance will eventually transfer to S. aureus. Since 1997, sporadic cases of vancomycin intermediate resistant S. aureus (VISA strains) have appeared. In these few cases resistance developed over time as a consequence of repeated exposure to vancomycin, and not the result of acquiring vanA or vanB resistance operons.

The potential for a major epidemic exists if S. aureus develops resistance to vancomycin. It is clear from this bacteria's ability to cause outbreaks in hospitals that its spread will be difficult to control even with effective therapy. Because of the presence of VISA strains and the concern over high-level vancomycin resistance, it is of utmost importance that an effective method of controlling the spread of S. aureus infection be developed.

On Mar. 5, 2000, the CBS Evening News reported that hospital acquired infections cost the United States health care system over $5 billion per year. An earlier Lewin Group Report estimates that S. aureus costs hospitals in New York City alone upwards of $400 million dollars per year to control. Currently, most hospital visits in the United States are paid for by Health Maintenance Organizations (HMOs). Extended patient stays caused by complications unrelated to the intended procedure, such as hospital acquired infections, are often not covered by the HMO's. These extra costs are paid for by the hospitals. Hospital acquired infections equate to extended patient stays and extended patient treatment. In one New York City hospital, the average stay is 9 days. Reducing hospital infection rates would reduce the length of patient stays, and thus save a significant amount of money for hospitals, HMO's and ultimately patients.

20-40% of people carry S. aureus nasally. Normally, the effects of S. aureus are benign and people generally live with it with no harm. However, people who are carrying S. aureus have the ability to infect others via transmission to otherwise sterile sites. In a hospital setting, health care workers can pick up the bacteria from a patient and act as a vector, transmitting the bacteria to other individuals. For example, when a person has surgery, a doctor who carries S. aureus nasally can infect the patient, or the patient can infect himself, even if the patient is otherwise healthy. S. aureus and other pathogenic bacteria can also contaminate inanimate objects such as a dialysis machine, or a bronchoscope. The contaminated objects provide the source of the infection.

When a patient acquires an infection in a hospital, typically an isolate of the bacteria will be taken from the patient and sent to a laboratory. The laboratory performs phenotypic tests to determine the species of the bacteria and its antibiotic susceptibility profile, which provides the physician a guide to the proper antibiotic therapy. Phenotypic tests examine the physical and biological properties of the cell, as opposed to genotypic tests, which evaluate the DNA content of the cell's genes.

Unfortunately, many bacteria develop resistance to the drugs that are used to fight them. As a result of the high levels of antibiotic usage, hospitals provide a selective environment to add in the spread of drug resistant bacteria. Bacterial infections get worse over time because the bacteria become more resistant to the drugs used to treat them. The more resistant the bacteria get, the harder they are to eradicate and the more they linger in the hospital.

Hospitals and health care facilities today live with a baseline level of nosocomial infections among patients. Hospitals do not take active steps to control nosocomial infections until a significant number of patients acquire infections within a short period of time. When this happens, the hospital may begin to worry that it has an outbreak problem on its hands. A source of infection inside the hospital such as a patient or a dialysis machine could be spreading a virulent strain of bacteria.

Unfortunately, by the time that the hospital realizes that it has an outbreak problem, the outbreak probably has already been underway for months. Thus the hospital will already have expended a significant cost fighting the spread of infection, and will have to expend additional resources to eradicate the infection from the hospital.

When the infection has already become rampant, the hospital may try to combat the outbreak by locating the source of the infection. The source could be a patient in the hospital, a health care worker, an animal, a contaminated object, such as a bronchoscope, a prosthetic device, the plumbing in a dialysis machine, or a myriad of other locations. It is thus very important that the hospital be able to locate the source of the infection.

The hospital can attempt to locate the source of infection by determining the path of transmission of the infection. The hospital can potentially determine the path of transmission by subspeciating the bacteria. One way to subspeciate bacteria is to analyze the bacteria's DNA. This is referred to as "molecular" typing, or genotyping. Over time, a bacteria's DNA mutates, producing changes in the bacteria's DNA. Two isolates of bacteria taken from two different patients may appear to have identical physical properties or "phenotypic" characteristics. However, a closer examination of the bacterial DNA might reveal subtle differences that demonstrate that the two isolates are actually different subspecies or clonal types. As an example, genotypic tests compare the DNA of a given gene from two or more organism, whereas phenotypic tests compare the expression of those genes.

If the hospital determines that many patients are acquiring infections of the same species, then the hospital may suspect that it has an outbreak problem. In some cases drug susceptibility testing will determine that strains are different and that an outbreak has not occurred. Unfortunately, many outbreaks are cause by multidrug resistant organisms and which can not be distinguished based on drug susceptibility results. In these cases, sub-speciation data is necessary to distinguish strain types. Molecular typing is one effective way to subspeciate these strains. For example, suppose a number of patients in the burn ward of a hospital over the course of several months acquire S. aureus infections. Molecular typing reveals that all of the S. aureus isolates taken from the patients belong to the same or highly similar subspecies. In this case, the hospital would determine that there is likely a single point source of infection in the burn ward. However, if all of the patients have very different subspecies of S. aureus, then the infection is likely not coming from a single source, but may be coming from multiple sources and the breakdown of infection control practices.

Rarely do hospitals perform molecular typing to subspeciate bacteria (i.e. a DNA analysis) because they lack the tools and expertise. Also, in the age of HMO care, preventive typing does not constitute direct patient care; it is infection control. However, in the long run, the hospital pays increased costs because patient stays are longer as a direct result of nosocomial infections.

One method of molecular typing that is sometimes used by hospitals to subspeciate bacterial isolates is pulsed-field gel electrophoresis (PFGE). PFGE produce a pattern indicative of the organization of the bacterial chromosome. By comparing PFGE patterns from multiple isolates, the hospital can subspeciate the bacteria. The PFGE process involves cutting the bacterial chromosomal DNA into multiple macro-fragments of varying sizes and molecular weights. An image-based pattern results after these fragments are separated by pulsed-field electrophoresis.

One problem with PFGE is that it is difficult to compare PFGE patterns. To compare whether two bacteria belong to the same subspecies requires comparing two PFGE images. Typically, an individual compares two PFGE images by subjectively eyeing the two images to determine if they look identical. Comparing two images by the human eye is very subjective, and frequently does not produce accurate results. It is similar to comparing two photographs or comparing pictures of fingerprints by eye. Computer digitization and software programs which perform analog image matching are available that somewhat aid this process. However, this software image matching is still a subjective science and does not provide sufficient biological criteria to evaluate the degree of relatedness between different strains. Additionally, image-based methods remain difficult to standardize between laboratories.

Another problem with PFGE is that there may be DNA mutations that do not affect the pulsed-field gel pattern. In these instances, two bacterial isolates may appear to have to have identical PFGE patterns, and yet, in reality, may be of different clonal types. PFGE is also a laborious and time consuming technique, and it is difficult to store PFGE images in a database because they take up too much memory.

A technique known as multilocus sequence typing (MLST) has been developed for Nesseira gonorrhea, Streptococcus pneumonia and Staphylococcus aureus, based on the classic multi-locus enzyme electrophoresis (MLEE) method that population biologists used to study the genetic variability of a species. MLST characterizes microorganisms by sequencing approximately 500 base-pair fragments from each of 9-11 housekeeping genes. The problem with the use of MLST in controlling infections in a rapid manner is that the MLST approach proves to be too labor intensive, too time consuming, and too costly to compare in a clinical setting. Over 5000 base pairs must be compared for each isolate. There is also limited genetic variability in the housekeeping gene targets and discrimination is therefore not adequately suitable for rapid infection control.

What is needed is a system and method for performing molecular typing in real time that can effectively and accurately subspeciate infectious agents. What is also needed is a system and method for typing infectious agents that are suitable for use with an electronic database and for communication of data over a computer network. What is also needed is a system that responds to an outbreak at a very early stage rather than beginning weeks or months after an outbreak has already begun. What is also needed is a system and method that can effectively speciate and subspeciate bacteria and determine relatedness among various subspecies in order to effectively track the path of transmission of the bacterial infection. What is also needed is a computerized and centralized system among hospitals and health care facilities that can accurately and quickly track the spread of infection regionally and globally as well as at the local hospital level.

SUMMARY OF THE INVENTION

The present invention is a system and method for performing real-time infection control over a computer network. The system of the present invention includes a computer network, an infection control facility having a server connected to the computer network, a centralized database accessible by the server. A number of health care facilities can communicate with the server via the computer network.

The method of the present invention includes first obtaining a sample of a microorganism at a health care facility. A first region of a nucleic acid from the microorganism sample is then sequenced. The sequencing can either be performed at the health care facility, or the sample can be physically sent to an infection control facility where the sequencing is performed. If the sequencing is performed at the health care facility, the sequence data is then transmitted to the infection control facility over a computer network or by other communication means. The first sequenced region is then compared with historical sequence data stored in a centralized database at the infection control facility. A measure of phylogenetic relatedness between the microorganism sample and historical samples stored in the centralized database is determined. The infection control facility then transmits infection control information based on the phylogenetic relatedness determination to the health care facility over the computer network, thereby allowing the health care facility to use the infection control information to control or prevent the spread of an infection.

The region of DNA that is sequenced has been identified to have a mutation rate that is suitably fast for performing real-time infection control. Regions of DNA that display repetitive motifs and patterns are often suitable as typing regions. In particular, the protein A gene (spa) and coagulase (coa) gene of Staphylococcus aureus, have been found to have a reliable "clock speed" for real-time infection control.

The determination of phylogenetic relatedness between two sequences can include determining a cost based on similarities in repeat motifs in the two sequences. The determination of phylogenetic relatedness between two sequences can also include determining a cost based on point mutations. A total cost can be determined based on a weighted combination of the repeat motif cost and the point mutation cost. When calculating a phylogenetic distance between two sequences, the deletion or insertion of a repeat sequence is treated as a single event. Point mutations are also treated as a single event.

The microorganism sample can be compared to historical samples obtained from the same health care facility. The microorganism sample can also be compared to historical samples obtained from the same geographical region. The microorganism sample can also be compared to historical samples obtained from anywhere in the world. In this way, the spread of the infection can be tracked on local, regional, and global levels.

Another feature of the invention includes transmitting the physical location or locations of the patient to the infection control facility, and determining a path of transmission of a microorganism based on the determined phylogenetic relatedness and the physical location of the patient. The centralized database can store a map of the health care facility, allowing the server to determine the spread of the infection based on the map. Patients can wear electronic identification devices that transmit their locations to the infection control facility, and allows patients to be electronically tracked.

Another feature of the present invention includes predicting the virulence and other properties of the sampled microorganism by retrieving the virulence data of similar microorganisms from the centralized database, and transmitting virulence information and other properties to the health care facility. Other properties of the microorganism can also be determined such as resistance to drugs, and drugs suitable for treatment.

Another feature of the present invention includes determining whether the health care facility has a potential outbreak problem, and transmitting an outbreak warning to the health care facility.

Additional regions of the nucleic acid of the microorganism sample can be sampled. Determinations of relatedness based on the additional sequenced regions can be performed to verify the determination of relatedness based on the first sequenced region, or to group various subspecies of bacteria into hierarchical levels. Additionally, slowly mutating regions of the nucleic acid can be used for tracking the long-term global spread of an infection, while faster mutating regions of the nucleic acid can be used for tracking the short-term local spread of an infection.

BRIEF DESCRIPTION OF THE DRAWINGS

FIGS. 7A and 7B depict examples of database records and the types of data that can be stored in a database record in a centralized database.

DETAILED DESCRIPTION OF THE INVENTION

The system and method of the present invention sequences one or more regions of the DNA of a microorganism and stores the DNA sequence data (A-T-C-G) in a centralized database. The DNA sequence data allows subspecies of the microorganism to be accurately identified and the relatedness with other subspecies can be effectively determined. Because the DNA sequence data is comprised of discrete units, as opposed to analog data, the DNA sequence data is highly portable and easily stored and analyzed in a relational database. Comparison of DNA sequence data between subspecies is objective, rapid and allows for accurate computer analysis. The system and method of the present invention can be applied to a variety of microorganisms and infectious agents such as bacteria, viruses and fingi. The system and method of the present invention is described below in more detail with respect to the figures.

Figure 1:
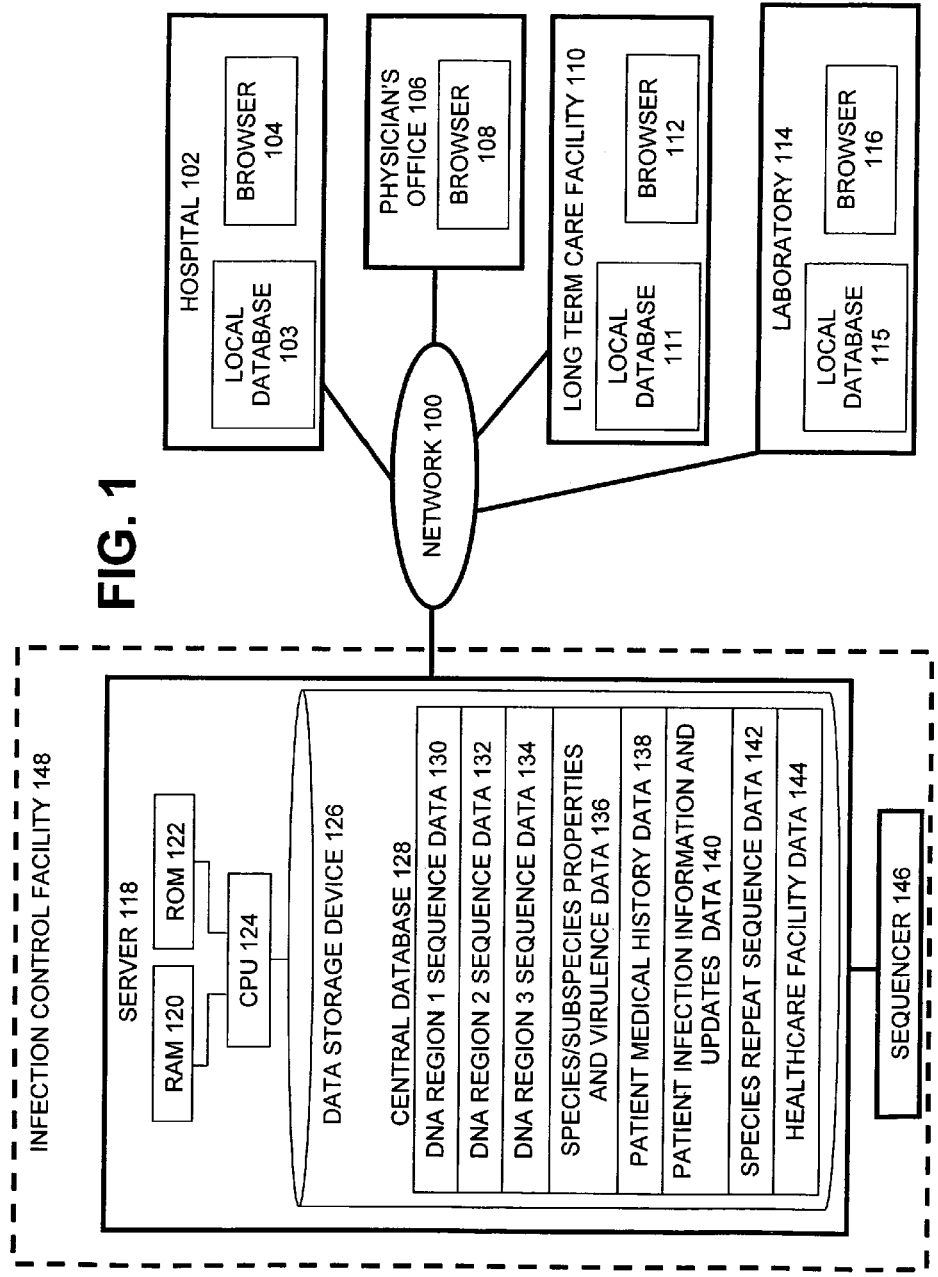
FIG. 1 depicts a block diagram illustrating a system architecture suitable for implementing the infection control system of the present invention.

FIG. 1 depicts a blocking diagram illustrating a system architecture suitable for implementing the infection control system of the present invention. As shown in FIG. 1, various terminals at a number of health care facilities such as hospital terminal 102, a physician's office terminal 106, long term care facility terminal 110, and laboratory terminal 114 all communicate with an infection control facility 148 via a network 100. Other institutions or entities involved in infection control can also connect to infection control facility 148 via network 100.

Network 100 can be any network connecting computers. Network 100 can be a wide area network (WAN) connecting computers such as the Internet. Network 100 could also be a local area network (LAN). Hospital terminal 102, physician's office terminal 106, long term care facility terminal 110, and laboratory terminal 114 operate browser programs 104, 108, 112 and 116, respectively.

Infection control facility 148 sequences predetermined regions of DNA from infectious isolates received from various health care facilities. Infection control facility 148 stores and analyzes the sequence data, tracks the spread of infections, and predicts infection outbreaks. Infection control facility 148 then informs the health care facilities of potential outbreak problems and provides infection control information. Other functions of infection control facility 148 will be described in more detail with respect to FIGS. 2-7.

Infection control facility 148 communicates with the local facilities via network 100. As an alternative to the use of a network, infection control facility 148 could communicate with the local facilities via alternative means such as fax, direct communication links, wireless links, satellite links, or overnight mail. Infection control facility 148 could also physically reside in the same building or location as the health care facility. For example, infection control facility 148 could be located within hospital 102. It is also possible that each of the remote health care facilities has its own infection control facility.

Infection control facility 148 includes a server 118 and a sequencer 146. Sequencer 146 sequences desired regions of DNA from infectious agents such as bacteria. The digital sequence data is then sent to server 118. Server 118 analyzes the digital sequence data and provides infection control information and warnings to hospital 102, physician's office 106, long term care facility 110, laboratory 114, and other facilities involved with infection control via network 100.

Server 118 contains a central processing unit (CPU) 124, a random access memory (RAM) 120, and a read only memory (ROM) 122. CPU 124 runs a software program for performing the method of the present invention described further below with respect to FIGS. 2-3.

CPU 124 also connects to data storage device 126. Data storage device 126 can be any magnetic, optical, or other digital storage media. As will be understood by those skilled in the art, server 118 can be comprised of a combination of multiple servers working in conjunction. Similarly, data storage device 126 can be comprised of multiple data storage devices connected in parallel.

Central database 128 is located in data storage device 126. Central database 128 stores digital sequence data received from sequencer 146. Central database 128 also stores various types of information received from the various health care facilities. CPU 124 analyzes the infection data stored in central database 128 for infection outbreak prediction and tracking. Some examples of the various types of data that are stored in central database 128 are shown in FIG. 1. These types of data are not exclusive, but are shown by way of example only.

DNA region 1 sequence data 130 stores the digital sequence data of a first desired sequenced region of the DNA of an infectious agent such as a bacterium, virus, or fungus. As will be described in more detail with respect to FIG. 2, when an infectious isolate is obtained from a patient, other individual, or a piece of equipment, a first desired region of the DNA is sequenced and stored in DNA region one sequence data 130. Similarly, DNA region 2 sequence data 132 stores the digital sequence data of a second desired sequenced region of the DNA of an infectious agent. DNA region 3 sequence data 134 stores the digital sequence data of a third desired sequenced region of the DNA of an infectious agent. Central database 128 can store any number of sequenced regions of the DNA, as will be discussed further with respect to FIGS. 2-3.

Different organisms will have different predetermined regions of their respective DNA that are sequenced. For example, an isolate of *S. aureus* bacteria will have different regions that are sequenced than an isolate of *E. facaelis*. Each type of bacteria or other infectious agent will have predetermined regions that are used for sequencing. The way that those predetermined regions are chosen is described in more detail with respect to FIG. 2, step 214.

Central database 128 also stores species/sub-species properties and virulence data 136. Data 136 includes various properties of different species and subspecies of infectious agents. For example, data 136 can include phenotypic and biomedical properties, effects on patients, resistance to certain drugs, and other information about each individual subspecies of microorganism.

Patient medical history data 138 contains data about patients such as where they previously have been hospitalized and the types of procedures that have been done. This type of data is useful in determining where a patient may have previously picked up an infectious agent, and determining how an infection may have been transmitted.

Patient infection information data 140 stores updated medical information pertaining to a patient who has obtained an infection. For example, data 140 could store that a particular patient acquired an infection in a hospital during heart surgery. Data 140 includes the time and the location that an infection was acquired. Data 140 also stores updated data pertaining to a patient's medical condition after obtaining the infection, for example, whether the patient died after three weeks, or recovered after one week, etc. This information is useful in looking for correlates between a disease syndrome and a strain subtype. Additional phenotypic assays to determine toxin production, heavy metal resistances and capsule subtypes, as examples, will also be added to the strain database and update properties and virulence data 136.

Species repeat sequence data 142 stores specific repeat sequences that have been identified for particular organisms in predetermined regions of the organism's DNA. These repeat sequences will be discussed more fully with respect to FIGS. 2-4.

Health care facility data 144 contains information about various facilities communicating with server 118 such as hospital 102, physician's office 106, and long term care facility 110. Health care facility data 144 contains such information as addresses, number of patients, areas of infection control, contact information and similar types of information. Health care facility data 144 can also include internal maps of various health care facilities. As will be described later, these maps can be used to analyze the path of the spread of an infection within a facility.

Some of the health care facilities also have local databases. FIG. 1 shows that hospital 102, long term care facility 110 and laboratory 114 include local databases 103, 111, and 115, respectively. The local databases can store local copies of selected infection control information and data contained in central database 128, so that the health care facility can access its local database for infection control information instead of having to access central database 128 via network 100. Accessing the local database can be useful for times when communication with the infection control facility 148 is unavailable or has been disrupted.

The local database can be used to store private patient information such as the patient's name, social security number. The health care facility can send a patient's infection information and medical history data to infection control facility without sending the patient's name and social security number. Only the health care facility's local database stores the patient's name and social security number and any other private patient information. This helps to maintain the patient's privacy by refraining from the patient's private information over the network.

Figure 2A:
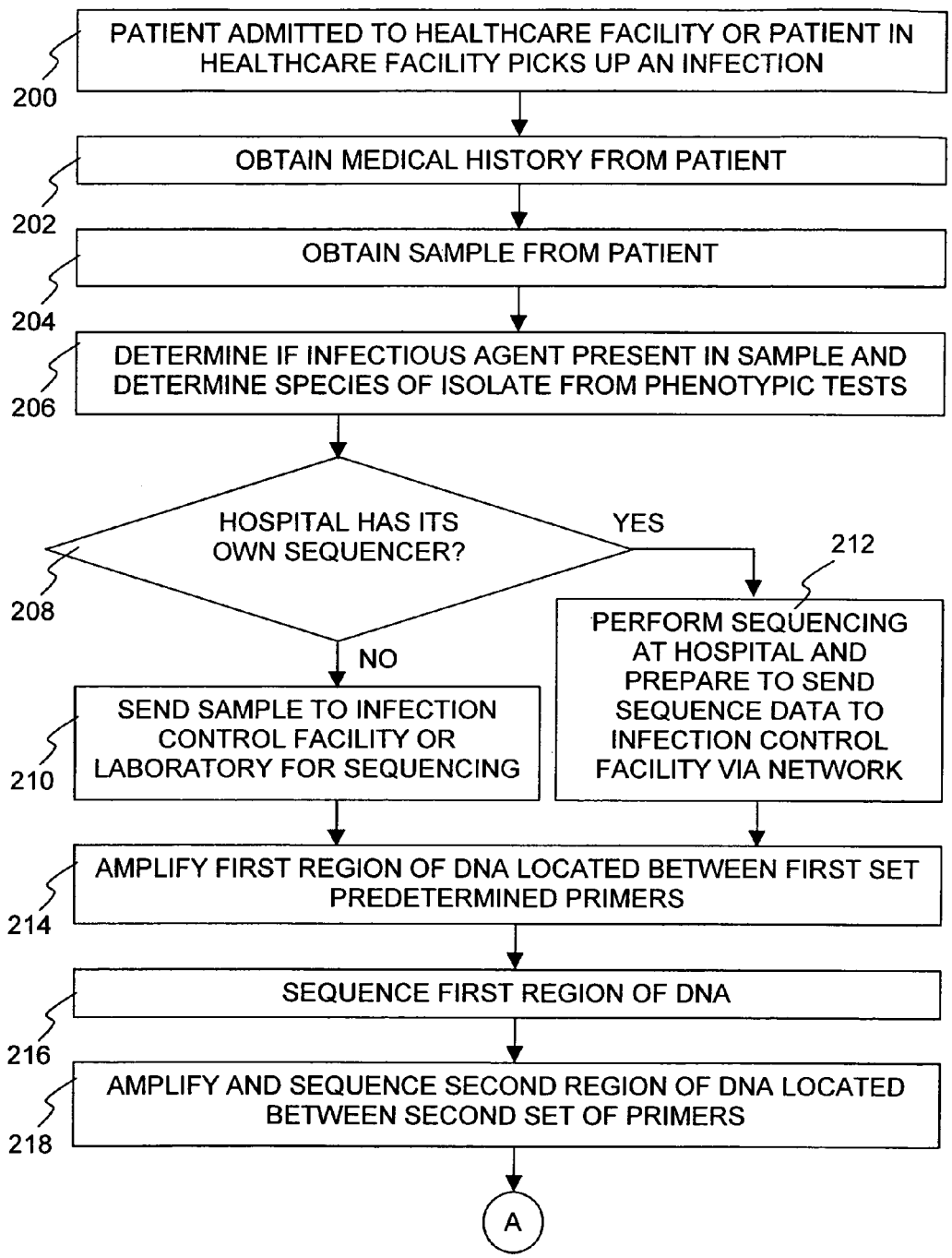
FIG. 2 depicts a flowchart illustrating a method of the present invention for performing infection control using the system architecture of FIG. 1.
Figure 2B:
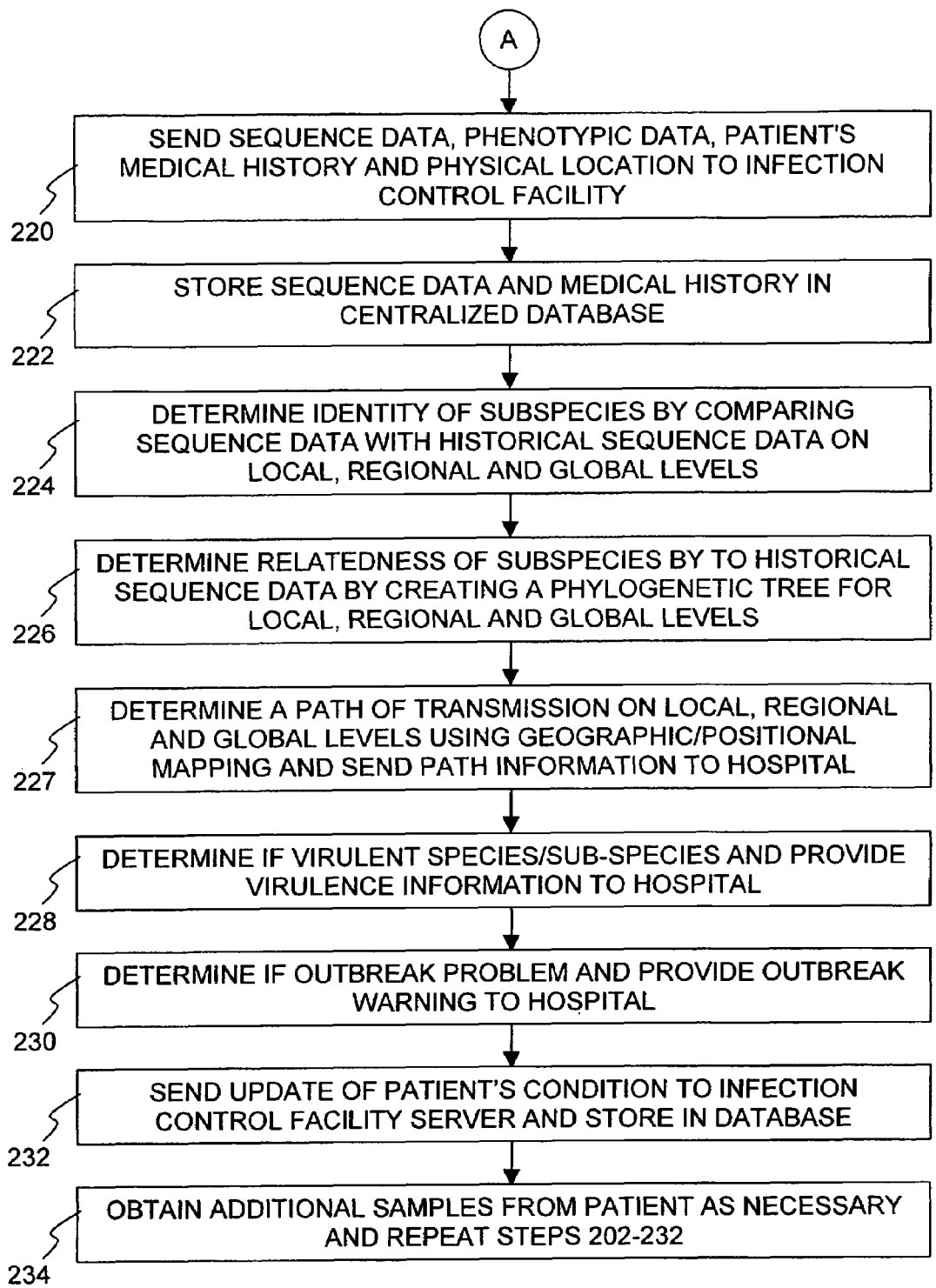

FIGS. 2 (2A and 2B) depicts a flowchart illustrating a method of the present invention for performing infection control using the system architecture of FIG. 1. In step 200, a patient is admitted to a health care facility such as a hospital. In step 202, a medical history is obtained from the patient. The medical history can be obtained by asking the patient a series of questions. The medical history will include factors that will determine the risk level of the patient for carrying a particular microorganism. For example, the patient can be asked whether he or she has been hospitalized recently, for how long, what kind of procedure, what foreign countries he or she has visited, etc. After obtaining the answers to these questions, the risk level of the patient for carrying a potentially infectious agent can be determined.

In step 204, a sample is taken from the patient. For example, the patient can be swabbed orally, nasally or rectally. In step 206, the sample is sent to a laboratory for analysis, such as laboratory 114 shown in FIG. 1. Laboratory 114 can be physically located in the same building as the health care facility. The laboratory determines whether an infectious organism is present in the sample. If an infectious organism is present, the laboratory performs phenotypic tests to determine the species of the organism.

The phenotypic tests performed in step 206 to determine the species of the microorganism are optional. The species of the microorganism can alternatively be determined from an analysis of the microorganism's DNA, as will be described further with respect to step 224.

A sample can be taken from a patient in step 204 every time that a patient in the health care facility acquires an infection. Alternatively, a sample can be taken from a patient in step 204 every time that a patient is admitted to the hospital or health care facility; i.e. a isolate is taken from every patient who is admitted regardless of whether they have an infection or have a high-risk of infection.

As an alternative method, a sample can be taken only from patients who are determined to have a high risk of infection (e.g. patients who have been hospitalized recently or traveled internationally recently).

Taking a sample from every patient when entering the health care facility might be too costly. On the other hand, this method catches the infection before the patient is admitted to the hospital, and thereby prevents introducing the infection into the hospital.

As will be described further with respect to step 234, the patient can also be sampled on a periodic basis or every time the patient is moved to a new location within a hospital or other facility. The patient's location when sampled is transmitted to server 118 and stored in central database 128. As will be described in more detail later, this allows server 118 to track the spread of an infection within a hospital or other facility, or within a geographic region, or globally.

In step 204, samples could be taken from objects instead of people. For example, a piece of equipment such as a dialysis machine might harbor microorganisms. A sample could be obtained from the dialysis machine.

In step 208, if the hospital has its own sequencer, then in step 212 the hospital performs its own sequencing of the organism's DNA. The digital sequence data is then transmitted electronically to infection control facility 148 via network 100. If the hospital does not have its own sequencer, then the samples are sent to infection control facility 148 for sequencing. Alternatively, the samples could be sent to a laboratory with a sequencer, such as laboratory 114, shown in FIG. 1. In this case, the laboratory 114 transmits the digital sequence data to infection control facility 148 via network 100.

Most hospitals today do not have their own sequencers. Therefore, in most cases the hospitals would send out their samples for analysis. However, in the future more and more hospitals will purchase their own sequencers. When this happens, all communications between the hospitals and infection control facility 148 can occur electronically via network 100. This will allow for rapid real-time infection control.

As mentioned previously, communications between infection control facility 148 and the hospitals can occur by alternative means other than a computer network, such as a direct communication link, a satellite link, a wireless link, overnight mail, fax, etc. Additionally, the infection control facility 148 could actually reside within the hospital, or the same building or facility as the hospital. In step 214, a first desired region of the DNA located between a first predetermined set of primers is then amplified by polymerase chain reaction (PCR) or similar technique. As will be understood by one skilled in the art, other types of nucleic acid besides DNA may be used, such as mRNA. In step 216, the amplified region of the DNA is then sequenced.

The region of the DNA that is sequenced has been predetermined to have desirable characteristics for infection tracking and control will now be described in more detail. The sequenced DNA is selected from the bacteria's (or other microorganism) chromosomal DNA or extrachromosomal DNA that is genetically variable; i.e. a region that is known to mutate. As an infection spreads, the bacterial infection gets passed from person to person or person to inanimate object. Over time, variability will be observed within a given species. Different organisms have different DNA regions that display genetic variability. The mutations result in polymorphisms in those regions of the organism's DNA. These polymorphisms provide an objective measurement to identify and track infectious organisms.

As bacteria cells reproduce, new generations of bacteria cells will contain new mutations (for the purposes of illustration, the discussion below will use the example of "bacteria;" however, the discussion applies to any microorganism). The more time that passes, the more the bacterial DNA will mutate. These mutations allow a path of infection to be traced. For example, if two patients A and B are both carrying bacteria that have identical DNA sequences in a predetermined region of the DNA, then it is likely that patient A transmitted the bacteria to patient B, or vice versa, or patient A and patient B both obtained the bacteria from the same source within a short time frame. If the predetermined region DNA sequences from the two bacterial isolates are very different then they are probably from different strains and it is unlikely that transmission occurred between the two patients. If the DNA from the two bacteria are somewhat similar, than it can be determined that the two patients may have picked up the infection in the same institution.

The goal behind sequencing the DNA is to distinguish epidemiologically related or clonal isolates, from unrelated isolates. Epidemiologically related isolates can be identified as being descendants from a common precursor cell, and as a consequence, their genomic "fingerprint" will be indistinguishable or similar from one another and recognizably different from unrelated or random isolates from the same species.

By analyzing the epidemiological relatedness of the DNA of various isolates of bacteria, a path of transmission of infection can be determined. By analyzing a region of the DNA that is known to mutate, the bacterial isolate can be identified and compared to other subspecies of bacteria. However, if the DNA region mutates too slowly, then all bacterial isolates will appear to be the same and it will be difficult to differentiate between different subspecies of the bacteria. On the other hand, if the region mutates too fast, then all of the bacteria will look extremely different and it will also be difficult to determine the path of transmission. Thus, the regions of the bacterial DNA which are chosen for sequencing are those regions with a good "clock speed"; i.e. regions that mutate not too fast and not too slow.

The DNA region which is chosen for sequencing must have a fast enough "clock speed" to allow real-time infection control within a health care facility to be performed. As described previously, the multilocus sequence typing (MLST) approach sequences many housekeeping genes which have limited genetic variability; i.e a slow clock speed. The slow clock speed of the MLST approach makes it unsuitable for real-time infection control. MLST approach is also too time consuming to perform in a real-time clinical setting. Over 5000 base pairs must be compared for each isolate.

One type of DNA region that has suitable variability for outbreak discrimination is a "repeat region." Repeat regions of the DNA feature repeating sequences of nucleotides. For example, in *S. aureus*, the polymorphic X region (also known as the $X_r$ region) of the protein A gene features repeat sequences of nucleotides usually 24 base pairs (bp) long. The $X_r$ region of the protein A gene of *S. aureus* has a variable length of variable number tandem repeats (VNTR).

Two *S. aureus* genes, protein A (spa) and coagulase (coa), both conserved within the species, have variable short sequence repeat (SSR) regions that are constructed from closely related 24 and 81 bp tandem repeat units, respectively. In both genes, the in-frame SSR units are degenerative, variable in number, and variable in the order the repeat units are organized. The genetic alterations in the SSR regions include both point mutations and intragenic recombination that arise by slipped-strand mispairing during chromosomal replication, and together this region shows a high degree of polymorphism.

Both the spa and the coa genes have been found to have a fast enough clock speed to be effective for use in real-time infection control. For example, the $X_r$ region of the spa gene can be sequenced in step 216. A study analyzing the use of the protein A gene as a typing tool was performed and is described in detail in the following article: B. Shopsin, M. Gomez, O. Montgomery, D. H. Smith, M. Waddington, D. E. Dodge, D. A. Bost, M. Riehman, S. Naidich, and B. N. Kreiswirth. "Evaluation of Protein A Gene Polymorphic Region DNA Sequencing for Typing of *Staphylococcus aureus* Strains", Journal of Clinical Microbiology, November 1999, p. 3556-3563. This article is incorporated by reference herein. This study found spa sequencing to be a highly effective rapid typing tool for *S. aureus* in terms of speed, ease of use, ease of interpretation, and standardization among laboratories.

320 isolates of *S. aureus* were typed by DNA sequence analysis of the X region of the protein A gene (spa). spa typing was compared to both phenotypic and molecular techniques for the ability to differentiate and categorize *S. aureus* strains into groups that correlate with epidemiological information. A collection of 59 isolates from the Centers for Disease Control and Prevention (CDC) was used to test for the ability to discriminate outbreak from epidemiologically unrelated strains. A separate collection of 261 isolates from a multicenter study of methicillin-resistant *S. aureus* in New York City was used to compare the ability of spa typing to group strains along clonal lines to that of the combination of PFGE and Southern hybridization. In the 320 isolates studies, spa typing identified 24 distinct repeat sequence types (also referred to herein as cassette types) and 33 different strain types (also referred to herein as subspecies). spa typing distinguished 27 of 29 related strains and did not provide a unique fingerprint for 4 unrelated strains from the four outbreaks of the CDC collection. In the NYC collection, spa typing provided a clonal assignment for 185 of 195 strains within the five major groups previously described.

The above study found that spa-typing was able to genotype the *S. aureus* isolates from two different collections and was suitably stable for epidemiological tracking. While spa-typing was found to have slightly less resolving power than PFGE sub-typing, spa-typing offers the advantages of speed, ease of use, ease of interpretation, and the ability to store in centralized database 128. Most significantly, DNA sequence analysis of the protein A repeat region provides an unambiguous, portable dataset that simplifies the sharing of information between laboratories and facilitates the creation of a large-scale database for the study of global as well as local epidemiology.

After a first desired region of DNA is sequenced, in step 218, a second region of the DNA can be amplified and sequenced. The second region of the DNA should also be a region with a desirable clock speed. Third, fourth, and additional regions may also be sequenced. At a minimum, only one region need be sequenced.

For reasons of speed and cost, it may be optimal for real-time infection control to sequence only a single region of the DNA. The disadvantage of sequencing more than one region is that the infection control method of the present invention becomes more costly and time consuming with each additional region sequenced. However, as described later in more detail, sequencing additional regions of the DNA can provide better confirmation of accurate typing and more discrimination. Therefore, as sequencing methods become cheaper and faster, it will become more desirable to sequence multiple regions of the DNA.

In step 220 the sequence data, phenotypic data, and patient's medical history and physical location are sent to infection control facility 148. In order to protect a patient's privacy, the health care facility does not need to send sensitive patient information such as the patient's name and social security number. As described previously, this information can be stored in a local database at the health care facility.

If the DNA was sequenced by a hospital, health care facility or laboratory, then the digital sequence data is transmitted to infection control facility 148 via network 100. Otherwise, the digital sequence data is obtained from sequencer 146.

In step 222, server 118 in infection control facility 148 stores the received sequence data and patient's medical history in centralized database 128. An example of a database record is described in more detail with respect to FIG. 7.

In step 224, server 118 attempts to determine the identity of the species and subspecies of the bacteria by comparing the DNA of the bacterial isolate with other historical DNA data stored in the database. The historical DNA is simply all of the previous isolate sequences that have been sent to server 118 and stored in centralized database 128.

In step 226, server 118 determines the relatedness of the bacterial isolate to other isolates stored in the database, by comparing the differences in the digital sequence data. The software of the present invention determines the relatedness of two isolates by comparing the similarities of the two sequences both on a base-pair level and on a "repeat motif" level, as will be described in more detail with respect to FIG. 3. A phylogenetic tree can then be created by determining the relatedness of the bacterial strains to other bacterial isolate DNA data stored in the database. The phylogenetic tree depicts the relatedness of each subspecies of bacteria to other subspecies, and thus reveals the path of transmission. "Phylogenetically closely related" means that the isolates are closely related to each other in an evolutionary sense, and therefore have significant similarities in their DNA. Organisms occupying adjacent and next to adjacent to positions on a phylogenetic tree are closely related.

Both steps 224 and 226 can be performed on local, regional, and global levels. For example, if a patient is admitted to a hospital in New York City, server 118 can compare the DNA from an isolate taken from that patient only with other isolates from that hospital. Alternatively, server 118 can compare the DNA only with other isolates taken from hospitals in New York City. Alternatively, server 118 can compare the DNA with other isolates taken from North America. In this way, in step 227, paths of transmission can be determined within a hospital, within a local region, within a broader region, or on a global scale.

Because the physical location of the patient when sampled is transmitted to server 118 and stored in database 128, server 118 can determine a path of transmission. The path of the spread of the infection can be determined in both time and space. Database 128 can also store a map of each internal health care facility. Server 118 can use this map to perform geographic/positional mapping of the spread of the infection. For example, server 118 could determine that an infection originated in the burn ward of a particular hospital, and then after one month, it spread to a cancer ward. Server 118 can also determine the spread of the infection on a regional and global scale. For example, server 118 could determine that an infection originated in a hospital in New York City and then spread to Boston, and then spread to Kansas.

Another feature of the present invention that can be used to assist in geographic/positional mapping and tracking the spread of infection is the use of electronic identification tags for each patient. Patients can be given electronic identification units when they enter a hospital or other facility, such as bar-coded tags, smart cards or some similar method of electronic identification. When patients are moved to a new location in the hospital, the patient uses his or her electronic identification device to gain admittance to each new room or ward. Alternatively, sensors are placed throughout the hospital that automatically track and register a patient's movement. This electronic positional data is then sent to a local computer at the health care facility and/or server 118 at infection control facility 148. This electronic data is used to track the patient's exact physical location as a function of time. This physical location data can be used to determine where the patient potentially acquired an infection, and the path of infection can be more easily determined.

In step 228, server 118 determines if the isolate taken from the patient is a virulent or dangerous strain. This can be determined from the virulence of identical or closely related strains. Central database 128 stores species/subspecies properties and virulence data 136 for various subspecies of bacteria. This data is used to distinguish between contaminating and infecting isolates and to distinguish between separate episodes of infection and relapse of disease. Data 136 links bacteria types with disease syndromes, such as cases of food poisoning and toxic shock syndrome. Data 136 can identify which subspecies are resistant to certain drugs, or which subspecies are treatable by certain drugs. Thus, central database 128 is able to link genetic markers and clinical presentations to identify important correlates of disease.

Server 118 can update properties and virulence data 136 based on medical data received from health care facilities. For example, if 90% of patients who acquired a certain subspecies of bacteria died from the infection, then the bacteria would be classified as virulent and dangerous. Hospitals can then be notified of the virulence and danger of the strain when a patient within the hospital acquires this kind of infection. Additionally, server 118 can determine whether the infectious agent is emanating from within the hospital or was introduced from outside of the hospital and notify the health care facility accordingly.

If an isolate sample is taken from a patient before admitting the patient to the hospital, the virulence of the isolate can then be determined before the patient is admitted to the hospital. If the patient is determined to have a virulent strain, the strain can be treated and eliminated before the patient is admitted, or extreme precautionary measures are taken, such as isolation of the patient. In this way, the hospital can prevent introducing the virulent strain into the hospital.

In step 230, server 118 can determine if the hospital or health care facility has a potential outbreak problem; i.e. whether the probability is high that a particular strain of microorganism is being transmitted to patients within the health care facility. For example, server 118 can determine that a hospital has had seven patients in the last month who have picked up the same or similar subspecies of *S. aureus*, and the infection is emanating from the burn ward. Server 118 then notifies the hospital that it may have an incipient outbreak occurring. The hospital can then take measures to correct the outbreak, and stop the infection from spreading before the outbreak ever gets a chance to begin. For example, the hospital might find that the infection is emanating from a sick patient in the burn ward, or a dialysis machine in the burn ward.

In step 232, the hospital or health care facility sends updates of a patient's condition to server 118. The updates are stored in the central database 128. For example, if a patient has acquired a strain of *S. aureus*, the patient's condition after each week or each day can be stored in central database 128. The database can store how long it took for the patient to recover or any other similar pertinent medical information. This information can then be used to determine the virulence of particular species and subspecies of bacteria.

In step 234, additional samples can be taken from the patient. Additional samples can be taken on a periodic basis, and/or whenever a patient is moved to a new location, and/or whenever the patient acquires an infection. Once a new sample is obtained, steps 206-232 are repeated. This improves the ability of server 118 to track and control infections spreading through the hospital.

Figure 3:
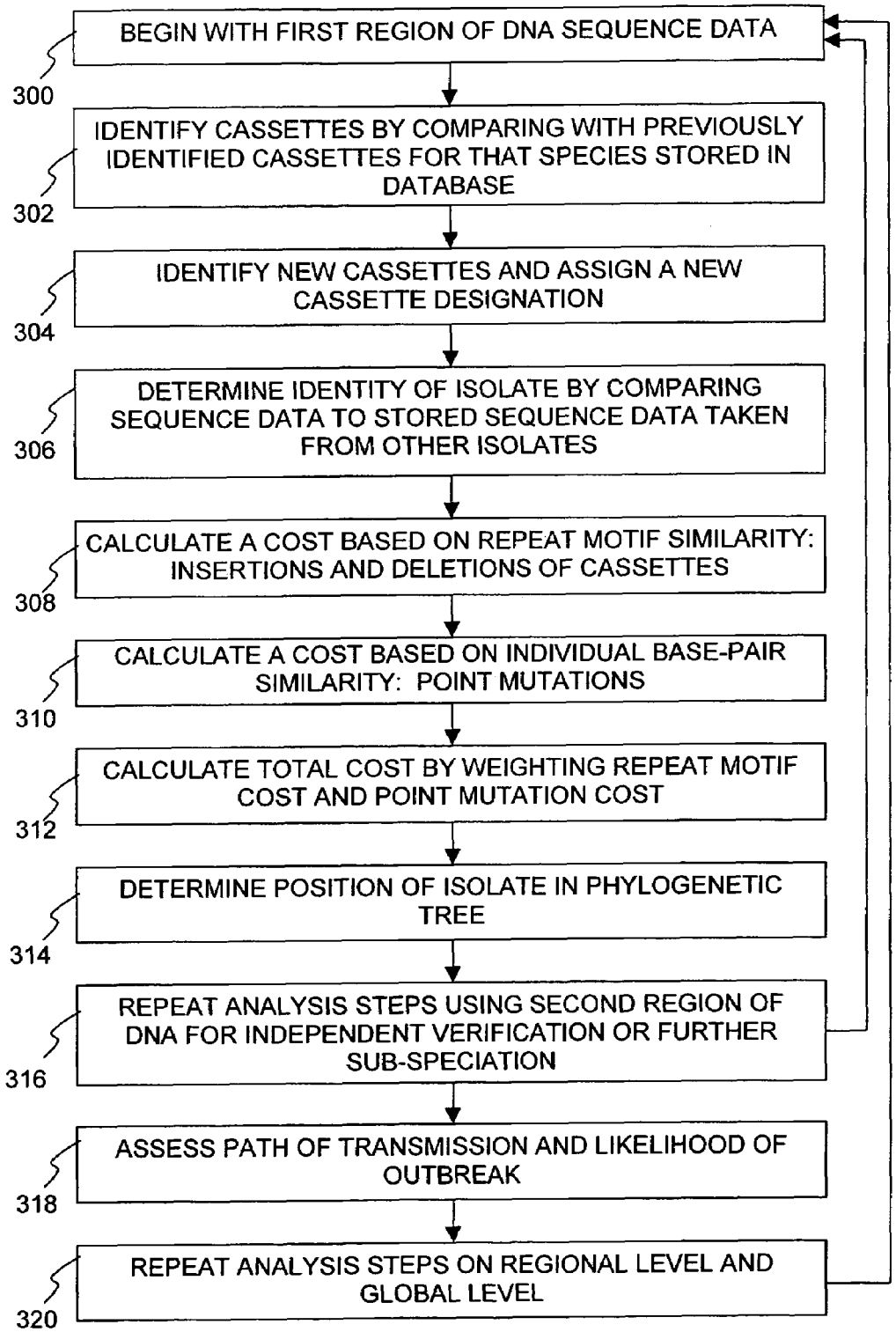
FIG. 3 depicts a flowchart illustrating a computer software method for determining relatedness between bacterial isolates.

FIG. 3 depicts a flowchart illustrating a computer software method for determining relatedness between bacterial isolates. In step 300, an analysis is begun of the first region of DNA that was sequenced in step 206 of FIG. 2. In step 302, "cassettes" or repeat sequences are identified. The terms "cassettes" and "repeat sequences" will be used interchangeably herein. The digital sequence data of individual nucleotides is then converted into cassette codes or designations.

Figure 4A:
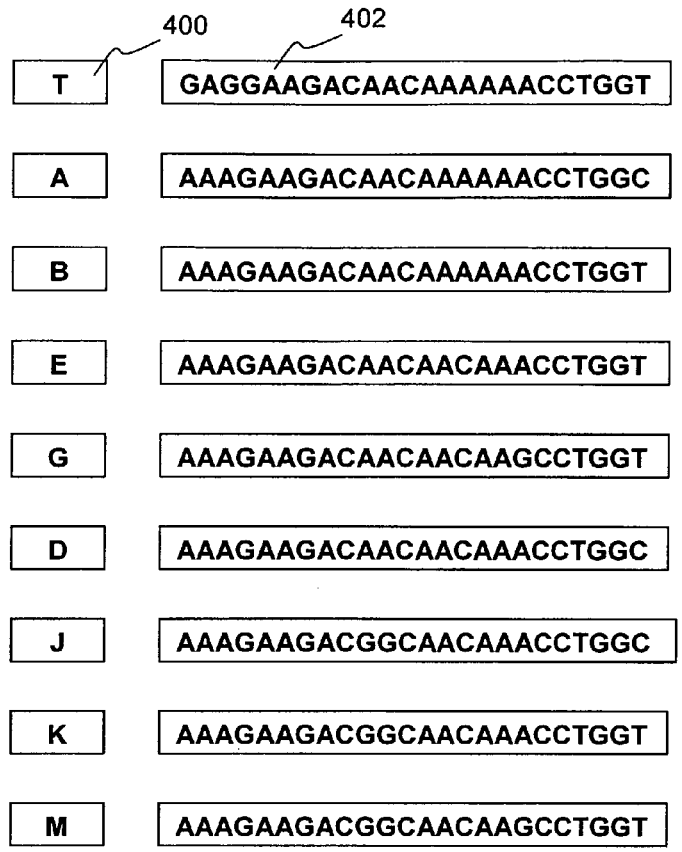
FIGS. 4A and 4B depict an example of how server 118 operating the software of the present invention converts raw nucleotide sequence data into repeat sequence designations.
Figure 4B:
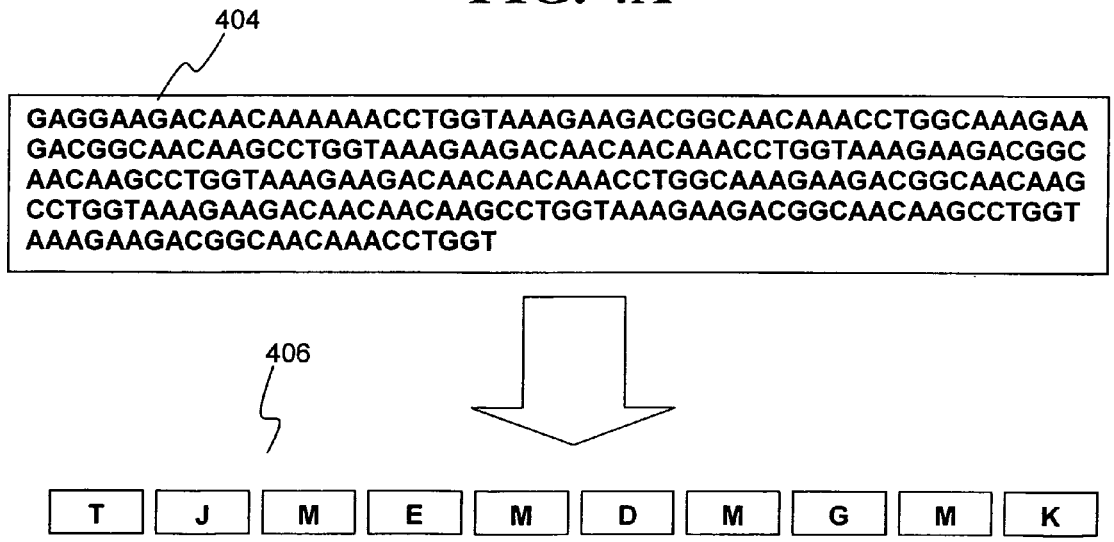

FIGS. 4A and 4B depict an example of how server 118 operating the software of the present invention converts raw nucleotide sequence data into repeat sequence designations. FIG. 4A shows nine different repeat sequences 402 that are each 24 base pairs long. These repeat sequences 402 are given as examples of repeat sequences which have been previously been found to occur in the $X_r$ region of the protein A gene for various isolates of *S. aureas*. Each one of these unique repeat sequences 402 is assigned a cassette designation 400 which in this example is simply a single letter code that represents the corresponding sequence. For example, the nine repeat sequences 400 shown in FIG. 4A are labeled 'T' SEQ ID NO: 1, 'A' SEQ ID NO: 2, 'B' SEQ ID NO: 3, 'E' SEQ ID NO: 4, 'G' SEQ ID NO: 5, 'D' SEQ ID NO: 6, 'J' SEQ ID NO: 7, 'K' SEQ ID NO: 8 and 'M' SEQ ID NO: 9. Other codes may be used besides a single letter, such as a combination of letters and numbers.

FIG. 4B depicts an example of a sequence 404 SEQ ID NO: 10 that was obtained by sequencing the $X_r$ region of the protein A gene of a bacterial isolate. The software scans the sequence data 404, identifies know repeat sequences, and converts the nucleotide data 404 into a string of cassette designations 406. A particular pattern of cassette designations 406 shows the following repeat motif: "TJMEMD-MGMK" SEQ ID NOS: 1, 7, 9, 4, 9, 6, 9, 5, 9, 8.

Returning to step 302, the DNA sequence for a bacterial isolate is analyzed by first identifying known previously identified repeat sequences for that species. For example, if the bacterial isolate is of species *S. aureus*, then the database will contain a listing of previously identified known repeat sequences for *S. aureus*. The individual nucleotide designations A, G, C, and Ts will be replaced by the cassette designations as shown in FIGS. 4A and 4B.

It is also possible that a bacterial isolate may contain some new repeat sequences that have never been previously identified. In this case, in step 304, the software scans the sequence data looking for new repeat sequences. If a new repeat sequence is found, it is assigned a new letter or code as a cassette designation.

At the conclusion of step 304, the repeat sequences have all been replaced with cassette designations. In step 306, server 118 attempts to determine the identity of the species/sub-species of the bacteria by comparing the DNA sequence with historical DNA sequences stored in the database and looking for a match.

In steps 308-314, the bacterial isolate's relatedness to other species/sub-species of bacteria is determined. The isolate's sequence data is compared to other sequence data stored in the database taken from other isolates. When comparing two isolates, the software compares the two isolates, and a relative "cost" is calculated. The relative cost is a measure of the phylogenetic relatedness or phylogenetic distance between the two sequences being compared. A low relative cost would indicate a low number of differences between the two sequences and hence a high degree of relatedness. A high relative cost would indicate a high number of difference between the two sequences, and hence a low degree of relatedness.

As an alternative to determining a relative cost between two isolates, an absolute cost could be calculated for each isolate. The absolute cost for an isolate can be calculated for each isolate by determining its phylogenetic distance from some predetermined reference sequence configuration. An absolute cost can be calculated for each individual isolate. The relatedness between isolates can then be determined based on comparison of their absolute costs. Thus, relative costs are generated by comparing sequences with each other, whereas absolute costs are generated by comparing each particular isolate with a reference configuration. Conventional software fails to effectively determine the relatedness of repeat regions of bacterial DNA for use as a real-time typing tool. Conventional software does not adequately determine relatedness between sequences because it does not adequately analyze the behavior of repeat regions. Repeat regions of bacterial DNA sometimes mutate by the insertions and deletions of whole cassettes. In the $X_r$ region of the protein A gene of *S. aureus*, a cassette is usually 24 base pairs long. A single 24 base pair cassette can be inserted or deleted by a single event.

The software of the present invention recognizes the insertion of a deletion of a single 24 base-pair length cassette as a single event, rather than 24 separate events. As an example, suppose the $X_r$ region of three bacterial isolates is sequenced. Sequence #1 is 72 base pairs long, sequence #2 is 144 base pairs long, and sequence #3 is 72 base pairs long. Conventional software would most likely find that sequence #1 and sequence #2 were not very related because of the difference in size of the sequence. Conventional software would treat the extra 72 base pairs as 72 point mutations. Conventional software would likely find that sequence #3 and sequence #1 were more closely related since they were the same size.

However, the software of the present invention might recognize that sequence #3 is simply sequence #1, with the insertion of 3 cassettes. Thus sequence #1 and sequence #3 might in fact be closely related, separated by only three events. Sequence #1 and sequence #3 could turn out to be more closely related than sequences #1 and #3 that are the same size. Thus, the software of the present invention treats an insertion or deletion of a cassette as a single event.

In step 308, two sequences are compared, and a relative cost is calculated based on the similarity of the repeat motifs. Analyzing repeat motifs involves looking at the number of insertions and deletions of whole cassettes, recognizes that the insertion or deletion of a cassettes is a single event, not 24 separate events. The software of the present invention in step 308 therefore compares the similarity of the two sequences based on the similarity of the repeat motifs, rather than only the similarity of the individual base-pairs. Thus, the relative cost calculated in step 308 is a measure of the similarity of the repeat motifs of the two sequences being compared.

As an alternative to comparing the two sequences directly, an absolute cost can be calculated for each sequence. The phylogenetic distance between the two species is then determined based on a comparison of the absolute costs.

In step 310, a point-mutation cost is calculated based on the similarity of individual base pairs, not on the basis of the repeat motif. For example, the insertion or deletion of a single A, G, C, or T in the sequence would constitute a single point mutation event.

In step 312, a total cost is calculated by summing the repeat-motif cost and the point mutation cost. The two costs may be weighted differently. The following equation could be used as a simple example for calculating an overall cost:

$D_{bp}$=# Deletions of a single nucleotide base-pair $I_{bp}$=# Insertions of a single nucleotide base-pair $D_{rep}$=Deletions of cassettes $I_{rep}$=# Insertions of cassettes $W_{dbp}$=weighting factor for deletions of individual base-pairs $W_{ibp}$=weighting factor for insertions of individual base-pairs $W_{drep}$=weighting factor for deletions of cassettes $W_{irep}$=weighting factor for insertions of cassettes Relatedness $R=W_{dbp}D_{bp}+W_{ibp}I_{bp}+W_{drep}D_{rep}+W_{irep}I_{rep}$ More advanced algorithms can be used for identifying similarities and costs when comparing repeat motifs and point mutations. For example, it can be determined that cassette A occasionally mutates into cassette B, but almost never mutates into cassette Z. Therefore, a change from cassette A to cassette B would be assigned a small predetermined cost, for example 10, and a change from cassette A to cassette Z would be assigned a large predetermined cost, for example 100.

Other weighting schemes can be employed based on the position of the cassette and order of the cassettes relative to one another. For instance, it may be found to be the case that for a particular species of bacteria, cassette A is sometimes followed by cassette B or cassette C but never cassette D in the first half of a repeat motif. Cassette A may be followed by cassette D in the second half of a repeat motif. Therefore weights can be relative to position and order.

Different weighting schemes can be used by analyzing the behavior of the microorganism sequences during its evolution. The key to these weighting schemes and determination of phylogenetic relatedness between strains is to break the sequences down into a repeat motifs and compare the sequences based on the similarity of the repeat motifs, not just the individual base-pairs.

After the costs are determined by comparing the isolate to a wide range of historical bacterial isolate data, in step 314, the position of the isolate in the phylogenetic tree is determined. This will allow for determination of the path of transmission of the bacteria.

In step 316, a second region of the DNA can be sequenced. This can be performed to independently verify the classification results obtained from analyzing the first DNA sequence region. It can also be used to further subspeciate the bacteria into hierarchical levels as described further with respect to FIG. 5. Steps 300-314 can be performed additional times for additional regions of the DNA if desired.

In step 318, the path of transmission of the bacteria can be determined based upon the position in the phylogenetic tree. For example, if a number of bacterial isolates have been emanating from the burn ward of a particular hospital, the hospital can be notified that it might have an outbreak problem. In step 320, the analysis steps 300-318 can be repeated on a regional level and a global level.

Figure 5:
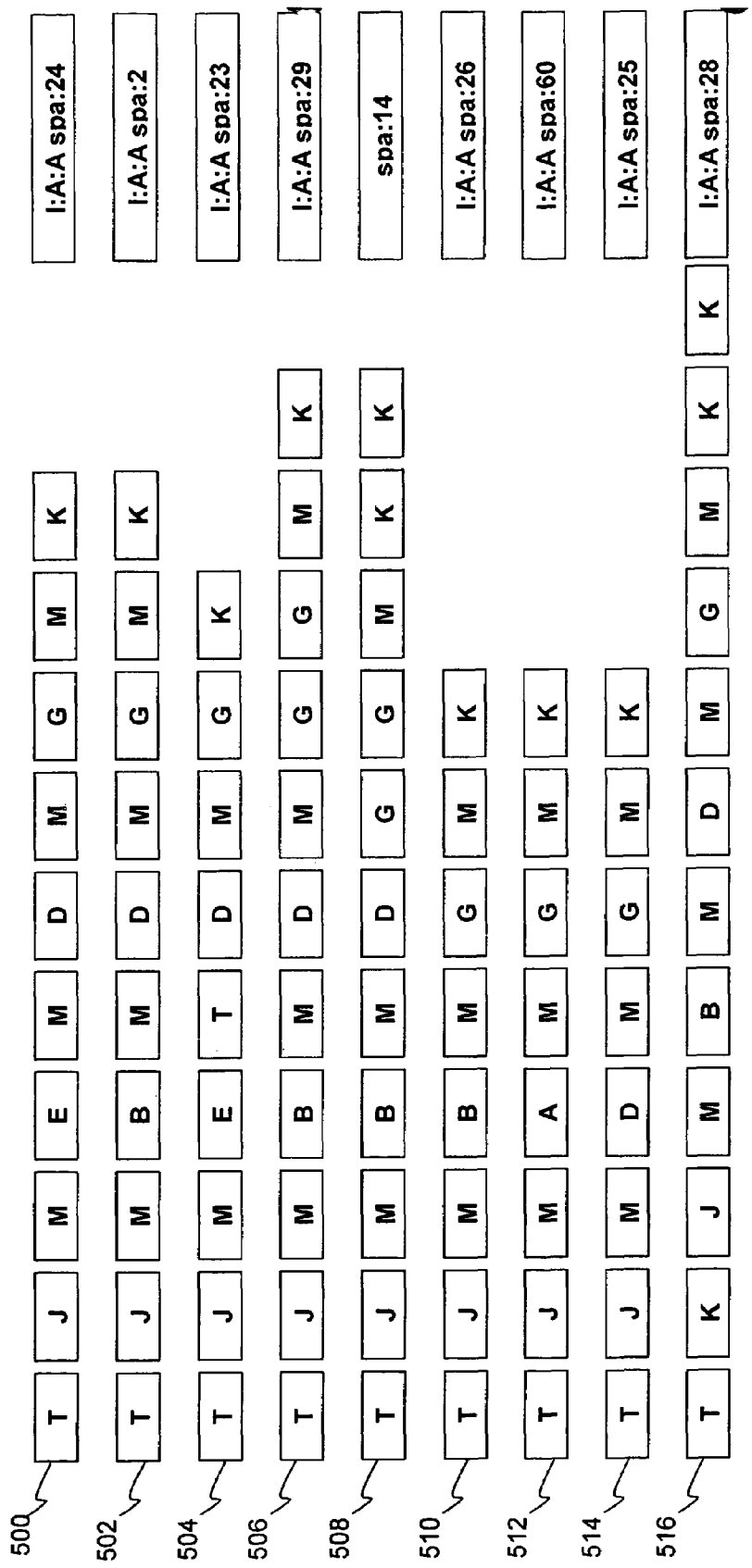
FIG. 5 depicts a block diagram illustrating an example of a series of isolate sequences that have been converted into repeat sequence designations.

FIG. 5 depicts a block diagram illustrating a series of isolates that has been converted into repeat sequence designations. Sequences 500-516 illustrates an example of a sequence that was obtained by sequencing the $X_r$ region of the protein A gene of an *S. aureus* isolate, and converted into repeat sequence designations. As can be seen, sequence 502 SEQ ID NOS: 1, 7, 9, 3, 9, 6, 9, 5, 9, 8 is identical to sequence 500 SEQ ID NOS: 1, 7, 9, 4, 9, 6, 9, 5, 9, 8 with the exception that the fourth cassette 'E' in sequence 500 has been replaced by a 'B'.

Conventional software would compare sequences 500 and 502 and determine a significant phylogenetic distance between sequences 500 and 502 due to the large number of differences in individual base-pairs. However, the software of the present invention would compare the repeat motifs of sequences 500 and 502, and thus recognize that the repeat motifs are very similar—only differing in a single repeat cassette.

Comparing sequences 504 SEQ ID NOS: 1, 7, 9, 4, 1, 6, 9, 5, 8 and 500: one 'M' cassette in sequence 500 has changed to a 'T' cassette in sequence 504, and one 'M' cassette in sequence 500 has been deleted. Thus, there are two discrete events separating sequences 504 and 500.

Comparing sequences 506 SEQ ID NOS: 1, 7, 9, 3, 9, 6, 9, 5, 5, 9, 8 and 500: one 'E' cassette in sequence 500 has changed to a 'B' cassette in sequence 506. So sequences 500 and 506 are separated by two discrete events.

Comparing sequences 502 and 506: only a single insertion of a single 'G' cassette. Thus sequences 502 and 506 are separated by only one discrete event.

The above analysis shows that sequences 502 and 506 are more closely related than sequences 500 and 506. A similar analysis can be performed to determine the relatedness between all of the sequences, and a phylogenetic tree can be constructed.

Figure 6:
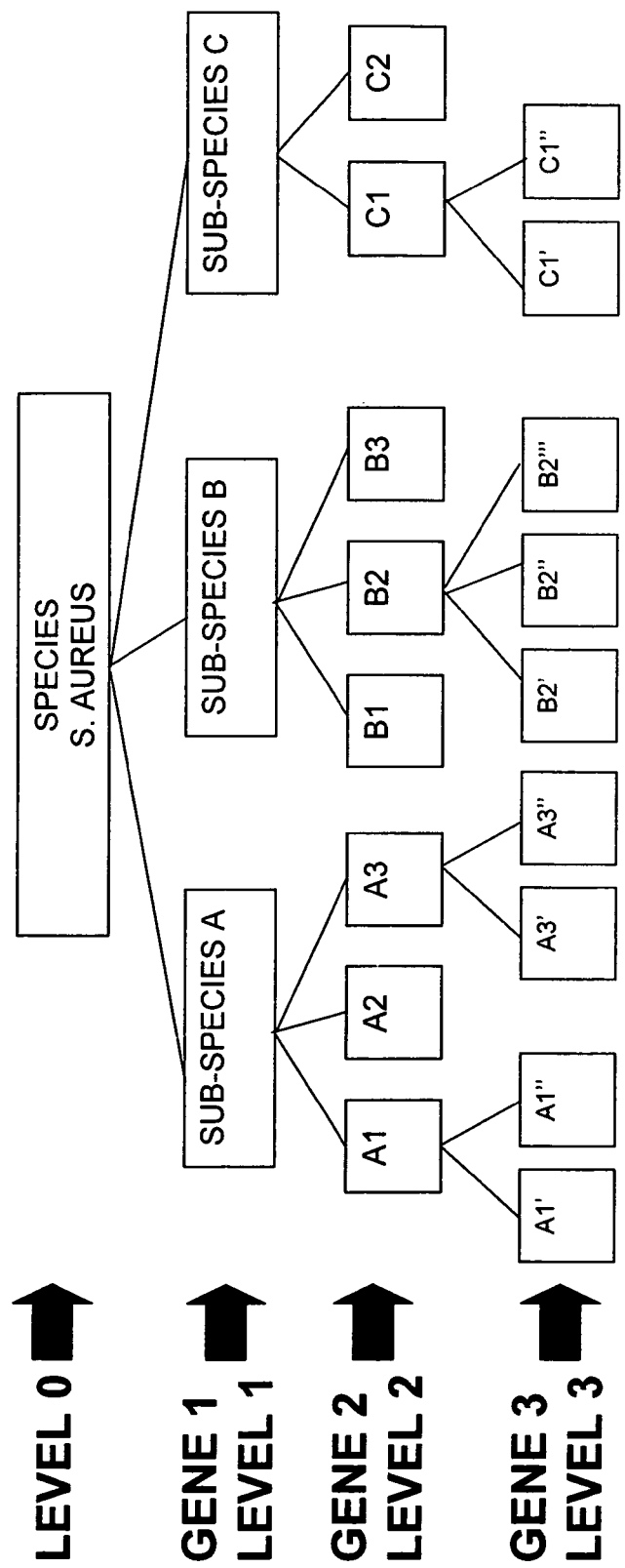
FIG. 6 depicts a block diagram illustrating how sequencing multiple regions of DNA allows the isolates to be grouped into hierarchical levels of subspeciation.

FIG. 6 depicts a block diagram illustrating how sequencing multiple regions of DNA allows the isolates to be grouped into hierarchical levels of subspeciation. Level zero is simply a determination of the species of the bacteria, for example, *S. aureus*. Sequencing a first gene, or region of the DNA, provides subspeciation of the bacteria into three different sub-species A, B, and C. Although FIG. 6 depicts the labels "GENE 1", "GENE 2", and "GENE 3" for simplicity, it will be understood by one of skill in the art that one may sequence any region of DNA or other nucleic acid that has predetermined desirable properties as described previously.

Sequencing gene 1 (or DNA region 1) provides a hierarchical level 1 of subspeciation. Level 1 can be further broken down into level 2 by sequencing a second gene, or region of DNA. Sequencing the second region of the DNA differentiates three sub-subspecies of subspecies A: A1, A2, and A3. Sequencing the second region of the DNA differentiates three sub-subspecies of subspecies B: B1, B2, and B3. Sequencing the second region of the DNA differentiates two sub-subspecies of subspecies C: C1 and C2.

Sequencing a third region of the DNA differentiates the level 2 subspecies into different level 3 subspecies. Sequencing the third region of the DNA differentiates two level three subspecies of level two subspecies A1: A1' and A1". Sequencing the third region of the DNA differentiates two level three subspecies of level two subspecies A3: A3' and A3". Sequencing the third region of the DNA differentiates three level three subspecies of level two subspecies B2: B2', B2", and B2'". Lastly, sequencing the third region of the DNA differentiates two level three subspecies of level two subspecies C1: C1' and C1".

This process illustrates that by sequencing multiple regions of the DNA, the bacteria can be classified into hierarchical levels of subspecies. This process is especially effective when gene 3 has a faster mutation rate than gene 2, which has a faster mutation rate that gene 1. Some genes may mutate too fast to be an effective tool, by themselves, for tracking infections. However, when sequenced in addition to other more slowly mutating genes, the information can be made useful by organizing the species into hierarchical levels as shown in FIG. 6.

Additionally, genes with slower rates of mutation are more suitable for long-term tracking of infections, such as tracking the global spread of an infection. Genes with faster rates of mutation are more suitable for short-term tracking of infections, such as tracking and controlling the real-time spread of an infection within a hospital.

FIGS. 7A and 7B illustrate some examples of database records and the types of data that can be stored in a database record in centralized database 148. FIG. 7A shows some examples of data fields pertinent to a microorganism sample that was taken from a patient. FIG. 7B shows an example of how the database stores previously identified repeat sequences for *S. aureus*.

Although the present invention has been described in terms of various embodiments, it is not intended that the invention be limited to these embodiments. Modification within the spirit of the invention will be apparent to those skilled in the art. For example, a touch-screen is not necessary. The customer can enter all selections by using a keyboard, keypad, voice commands, or any other input device. The scope of the present invention is defined by the claims that follow.

The invention claimed is:

1. A method of tracking the spread of infectious bacteria, comprising:

obtaining a plurality of bacterium samples from a plurality of patients or objects at a plurality of different physical locations;

performing DNA sequencing on a first region of deoxyribonucleic acid from each bacterium sample, the first region consisting essentially of a variable number of tandem repeats (VNTRs) region;

storing in a database for each of the plurality of bacterium samples: a) the nucleotide sequence data from the first sequenced region of each bacterium sample, and b) the physical location of the patient or object from which each bacterium sample was obtained;

comparing the nucleotide sequence data stored in the database of at least two of the plurality of samples on both a base pair level and a repeat motif level;

determining a measure of phylogenetic relatedness between the compared samples based upon differences between the compared nucleotide sequence data;

identifying patients infected or objects contaminated with phylogenetically related bacteria based on the phylogenetic relatedness determination;

tracking the spread over time of the bacteria based on: a) the identified patients or contaminated objects, and b) the physical locations of the identified patients or objects stored in the database; and providing a warning based on the tracking of the spread of the bacteria wherein the warning allows the recipient of the warning to control the further spread of the bacteria.

2. The method of claim 1, wherein the database is a centralized database located at a different location from where the sample is obtained.

3. The method of claim 1, wherein the database is located in the same location as where the sample is obtained.

4. The method of claim 1, wherein the first region that is sequenced is a region having a mutation rate sufficient to differentiate between subspecies to determine phylogenetic relatedness and to track the bacteria.

5. The method of claim 1, wherein the bacterium is *Staphylococcus aureus* and the first region is located in the protein A gene or the coagulase gene.

6. The method of claim 1, wherein each bacterium sample is obtained from a patient as the patient is admitted to a health care facility and prior to being exposed to patients in the health care facility.

7. The method of claim 1, further comprising:

obtaining a medical history from a patient from which at least one of the plurality of bacterium samples was taken;

determining an infection risk factor based on the patient's medical history, the infection risk factor being a measure of the patient's risk of acquiring an infection; and taking appropriate infection control measures in accordance with the infection risk factor.

8. The method of claim 7, further comprising:

segregating the information contained within the patient's medical history into private information and non-private information;

transmitting the patient's non-private information to the database without transmitting the patient's private information; and storing the patient's private information in a database at a different location from the database to which the patient's non-private information is transmitted.

9. The method of claim 1, wherein the step of performing DNA sequencing comprises either:

a) sequencing the first region at a physically separate facility and transmitting the resulting nucleotide sequence data to the database via a computer network; or b) sending each of the plurality of bacterium samples to an infection control facility that has access to the database, sequencing the first region at the infection control facility, and storing the nucleotide sequence data in the database.

10. The method of claim 1, wherein the first region is identified by a set of primers.

11. The method of claim 1, wherein the first region is amplified prior to DNA sequencing.

12. The method of claim 1, wherein the step of determining the phylogenetic relatedness between at least two compared samples comprises:

identifying repeat sequences in the nucleotide sequence data from each sample; and treating the insertion or deletion of a repeat sequence as a single genetic event.

13. The method of claim 1, wherein the step of determining the phylogenetic relatedness between at least two compared samples comprises:

identifying individual single nucleotide polymorphisms in the nucleotide sequence data from each sample; and treating an insertion or deletion or change of an individual nucleotide as a single genetic event.

14. The method of claim 1, wherein the step of determining the phylogenetic relatedness between at least two compared samples comprises at least one of:

comparing a first bacterium sample to other samples obtained from the same location as where the first bacterium sample was taken, thereby determining a local phylogenetic relatedness;

comparing the first bacterium sample to other samples obtained from the same geographical region as where the first bacterium sample was taken, thereby determining a regional phylogenetic relatedness; and comparing the first bacterium sample to other samples obtained globally, thereby determining a global phylogenetic relatedness.

15. The method of claim 1, wherein the steps of storing nucleotide sequence data in a database and tracking the spread of the infection further comprises:

transmitting over a computer network the nucleotide sequence data from the first sequenced region of each of the plurality of bacterium samples and the physical location of the patient or object from which each bacterium sample is taken.

16. The method of claim 15, further comprising:

storing in the database a map of the physical location of where the plurality of samples were obtained; and determining the spread of the infection based on the map.

17. The method of claim 16, further comprising:

determining, via sensor, the patient's physical location prior to transmitting the patient's physical location.

18. The method of claim 1, further comprising:

determining the virulence of the bacterium by retrieving the virulence data of identical or similar bacteria from the database; and transmitting over a computer network virulence information to a location where the bacterium sample was obtained.

19. The method of claim 1, further comprising:

determining drug resistance and treatment information of the bacterium by retrieving drug information data of identical or similar bacteria from the database; and transmitting over a computer network the drug information data to a location where the bacterium sample was obtained.

20. The method of claim 1, wherein providing a warning comprises:

determining whether a location where each bacterium was obtained has an outbreak problem; and transmitting over a computer network an outbreak warning to each location having an outbreak problem.

21. The method of claim 1, further comprising:
performing DNA sequencing on a second region of deoxyribonucleic acid of each bacterium sample;
storing the nucleotide sequence data from the second region of the deoxyribonucleic acid of each bacterium sample in a database;
comparing the nucleotide sequence data from the second sequenced region to nucleotide sequence data already stored in the database; and
determining a measure of phylogenetic relatedness based on the comparison of the first and second sequenced regions.

22. The method of claim 21, wherein the determination of relatedness based on the second sequenced region is used to verify the determination of relatedness based on the first sequenced region.

23. The method of claim 21, further comprising:
identifying a first level of subspecies of each bacterium sample based on the first sequenced region; and
identifying a second level of subspecies of each bacterium sample based on the second sequenced region.

24. The method of claim 21, further comprising:
tracking the global spread of an infection based on the sequencing and comparing a slowly mutating region of the deoxyribonucleic acid; and
tracking the local spread of an infection based on the sequencing and comparing a more rapidly mutating region of the deoxyribonucleic acid.

25. A system for tracking the spread of infectious bacteria, comprising:
a computer network;
a centralized database;
a facility, connected to the computer network, where a plurality of bacterium samples from a plurality of patients or objects at a plurality of different locations are obtained;
a server connected to the computer network, the server receiving nucleotide sequence data for a first sequenced region of a deoxyribonucleic acid from each of the plurality of bacterium samples and a physical location of a patient or object from which each bacterium sample was obtained, the first sequenced region consisting essentially of a variable number of tandem repeats (VNTRs) region;
storing in a database for each of the plurality of bacterium samples: a) the nucleotide sequence data from each of the plurality of bacterium samples, and b) the physical location of the patient or object from which each bacterium sample was obtained;
accessing the centralized database and comparing the stored nucleotide sequence data of at least two of the plurality of bacterium samples;
determining a measure of phylogenetic relatedness between the compared samples;
identifying patients infected or objects contaminated with phylogenetically related bacteria based on the phylogenetic relatedness determination;
tracking the spread over time of the bacteria based on a) the identified patients or objects, and b) and the physical locations of the identified patients or objects stored in the database; and
transmitting a warning over the computer network to the facility based on the tracking of the spread of the bacteria, thereby allowing the facility to control further spread of the bacterial infection.

26. Computer-executable software code stored on a computer-readable medium for performing the method according to claim 1, wherein said spread of infectious bacteria is tracked using a computer network.

27. The method of claim 1, wherein the plurality of bacterium samples are obtained at a location physically separate from where the DNA sequencing is performed.

28. The method of claim 27, wherein the physically separate location is a health care facility, and the sample of the bacterium is obtained from a patient as the patient is admitted to a health care facility and prior to being exposed to patients in the health care facility.

29. The method of claim 1, wherein the sample is obtained at a location physically separate from where the DNA sequencing, comparing, and determination of a measure of phylogenetic relatedness occurs.

30. The method according to claim 1, wherein what may be an outbreak of bacterial infection is confirmed or refuted based upon the determination of phylogenetic relatedness.

31. The system of claim 25, wherein the DNA sequencing occurs at the facility and further wherein the nucleotide sequence data is transmitted over the computer network to the server.

32. The system of claim 25, wherein the step of determining the phylogenetic relatedness between at least two compared samples comprises:
identifying repeat sequences in the nucleotide sequence data from each sample; and treating the insertion or deletion of a repeat sequence as a single genetic event.

33. The system of claim 25, wherein the step of determining the phylogenetic relatedness between at least two compared samples comprises:
identifying individual single nucleotide polymorphisms in the nucleotide sequence data from each sample; and treating the insertion or deletion or change of an individual nucleotide as a single genetic event.

* * * * *

SEQUENCE LISTING

<160> NUMBER OF SEQ ID NOS: 22

<210> SEQ ID NO 1
<211> LENGTH: 24
<212> TYPE: DNA
<213> ORGANISM: Staphylococcus aureus

<400> SEQUENCE: 1
gaggaagaca acaaaaaacc tggt                                              24

<210> SEQ ID NO 2
<211> LENGTH: 24
<212> TYPE: DNA
<213> ORGANISM: Staphylococcus aureus

<400> SEQUENCE: 2
aaagaagaca acaaaaaacc tggc                                              24

<210> SEQ ID NO 3
<211> LENGTH: 24
<212> TYPE: DNA
<213> ORGANISM: Staphylococcus aureus

<400> SEQUENCE: 3
aaagaagaca acaaaaaacc tggt                                              24

<210> SEQ ID NO 4
<211> LENGTH: 24
<212> TYPE: DNA
<213> ORGANISM: Staphylococcus aureus

<400> SEQUENCE: 4
aaagaagaca acaacaaacc tggt                                              24

<210> SEQ ID NO 5
<211> LENGTH: 24
<212> TYPE: DNA
<213> ORGANISM: Staphylococcus aureus

<400> SEQUENCE: 5
aaagaagaca acaacaagcc tggt                                              24

<210> SEQ ID NO 6
<211> LENGTH: 24
<212> TYPE: DNA
<213> ORGANISM: Staphylococcus aureus

<400> SEQUENCE: 6
aaagaagaca acaacaaacc tggc                                              24

<210> SEQ ID NO 7
<211> LENGTH: 24
<212> TYPE: DNA
<213> ORGANISM: Staphylococcus aureus

<400> SEQUENCE: 7
aaagaagacg gcaacaaacc tggc                                              24

<210> SEQ ID NO 8
<211> LENGTH: 24
<212> TYPE: DNA

```
<400> SEQUENCE: 8
aaagaagacg gcaacaaacc tggt                                        24

<210> SEQ ID NO 9
<211> LENGTH: 24
<212> TYPE: DNA
<213> ORGANISM: Staphylococcus aureus

<400> SEQUENCE: 9
aaagaagacg gcaacaagcc tggt                                        24

<210> SEQ ID NO 10
<211> LENGTH: 240
<212> TYPE: DNA
<213> ORGANISM: Staphylococcus aureus

<400> SEQUENCE: 10
gaggaagaca acaaaaaacc tggtaaagaa gacggcaaca aacctggcaa agaagacggc    60
aacaagcctg gtaaagaaga caacaacaaa cctggtaaag aagacggcaa caagcctggt   120
aaagaagaca caacaaaacc tggcaaagaa gacggcaaca agcctggtaa agaagacaac   180
aacaagcctg gtaaagaaga cggcaacaag cctggtaaag aagacggcaa caaacctggt   240

<210> SEQ ID NO 11
<211> LENGTH: 10
<212> TYPE: DNA
<213> ORGANISM: Staphylococcus aureus

<400> SEQUENCE: 11
attcatagat                                                        10

<210> SEQ ID NO 12
<211> LENGTH: 10
<212> TYPE: DNA
<213> ORGANISM: Staphylococcus aureus

<400> SEQUENCE: 12
cgtactatcc                                                        10

<210> SEQ ID NO 13
<211> LENGTH: 10
<212> TYPE: DNA
<213> ORGANISM: Staphylococcus aureus

<400> SEQUENCE: 13
attcgttata                                                        10

<210> SEQ ID NO 14
<211> LENGTH: 10
<212> TYPE: DNA
<213> ORGANISM: Staphylococcus aureus

<400> SEQUENCE: 14
attaatagat                                                        10

<210> SEQ ID NO 15
<211> LENGTH: 10
<212> TYPE: DNA
<213> ORGANISM: Staphylococcus aureus

<400> SEQUENCE: 15
cgtactatcc                                                        10
```

```
<210> SEQ ID NO 16
<211> LENGTH: 10
<212> TYPE: DNA
<213> ORGANISM: Staphylococcus aureus

<400> SEQUENCE: 16
attcgttata                                                          10

<210> SEQ ID NO 17
<211> LENGTH: 12
<212> TYPE: DNA
<213> ORGANISM: Staphylococcus aureus

<400> SEQUENCE: 17
aattcgccta gg                                                       12

<210> SEQ ID NO 18
<211> LENGTH: 12
<212> TYPE: DNA
<213> ORGANISM: Staphylococcus aureus

<400> SEQUENCE: 18
aattccccta gg                                                       12

<210> SEQ ID NO 19
<211> LENGTH: 8
<212> TYPE: DNA
<213> ORGANISM: Staphylococcus aureus

<400> SEQUENCE: 19 taggccgt                                                             8

<210> SEQ ID NO 20
<211> LENGTH: 12
<212> TYPE: DNA
<213> ORGANISM: Staphylococcus aureus

<400> SEQUENCE: 20
ttaaaggcct ga                                                       12

<210> SEQ ID NO 21
<211> LENGTH: 12
<212> TYPE: DNA
<213> ORGANISM: Staphylococcus aureus

<400> SEQUENCE: 21
ggttccaata at                                                       12

<210> SEQ ID NO 22
<211> LENGTH: 8
<212> TYPE: DNA
<213> ORGANISM: Staphylococcus aureus

<400> SEQUENCE: 22 ggttaacc                                                             8
```